United States Patent
Boukhny et al.

(10) Patent No.: US 9,681,947 B2
(45) Date of Patent: Jun. 20, 2017

(54) INTRAOCULAR LENS DELIVERY SYSTEM WITH TEMPERATURE CONTROL

(75) Inventors: Mikhail Boukhny, Laguna Niguel, CA (US); James Chon, Irvine, CA (US); David Downer, Fort Worth, TX (US); Steve Van Noy, SouthLake, TX (US)

(73) Assignee: NOVARTIS AG, Basel (CH)

( * ) Notice: Subject to any disclaimer, the term of this patent is extended or adjusted under 35 U.S.C. 154(b) by 1388 days.

(21) Appl. No.: 11/584,996

(22) Filed: Oct. 23, 2006

(65) Prior Publication Data

US 2008/0097460 A1    Apr. 24, 2008

(51) Int. Cl.
*A61F 9/00* (2006.01)
*A61F 2/16* (2006.01)

(52) U.S. Cl.
CPC .................... *A61F 2/1662* (2013.01)

(58) Field of Classification Search
USPC .......................................... 606/107; 623/6.12
See application file for complete search history.

(56) References Cited

U.S. PATENT DOCUMENTS

| | | | |
|---|---|---|---|
| 4,053,953 A * | 10/1977 | Flom et al. | 623/6.38 |
| 4,198,980 A | 4/1980 | Clark | |
| 4,214,585 A | 7/1980 | Bailey, Jr. | |
| 4,573,998 A | 3/1986 | Mazzocco | |
| 4,600,003 A | 7/1986 | Lopez | |
| 4,681,102 A | 7/1987 | Bartell | |
| 4,747,404 A | 5/1988 | Jampel et al. | |
| 4,834,094 A | 5/1989 | Patton et al. | |
| 4,917,680 A | 4/1990 | Poley | |
| 4,919,130 A | 4/1990 | Stoy et al. | |
| 4,955,889 A * | 9/1990 | Van Gent | 606/107 |
| 4,988,352 A | 1/1991 | Poley | |
| 5,176,686 A | 1/1993 | Poley | |
| 5,190,552 A | 3/1993 | Kelman | |
| 5,275,604 A | 1/1994 | Rheinish et al. | |
| 5,304,182 A | 4/1994 | Rheinish et al. | |
| 5,494,484 A | 2/1996 | Feingold | |
| 5,616,148 A | 4/1997 | Eagles et al. | |
| 5,620,450 A | 4/1997 | Eagles et al. | |
| 5,653,715 A | 8/1997 | Reich et al. | |
| 5,716,364 A | 2/1998 | Makker et al. | |
| 5,728,102 A | 3/1998 | Feingold et al. | |
| 5,735,858 A | 4/1998 | Makker et al. | |

(Continued)

FOREIGN PATENT DOCUMENTS

| | | |
|---|---|---|
| CA | 2667450 | 9/2008 |
| EP | 1 360 944 A2 | 11/2003 |

(Continued)

OTHER PUBLICATIONS

International Search Report for PCT/US2007/082195, Publication No. WO2008/105965, Dated Oct. 6, 2008, 3 pages.

PCT International Preliminary Report on Patentability and Written Opinion of the International Searching Authority, International Application No. PCT/US07/082181, Filed Oct. 23, 2007, Publication No. WO/2008/143690, Published Nov. 27, 2008, report dated Apr. 28, 2009, 5 pages.

*Primary Examiner* — Julie A Szpira

(57) ABSTRACT

An intraocular lens delivery system has an injector body, a plunger, a nozzle portion, and a heater. The plunger is slidably movable within the injector body. The nozzle portion is located on a distal end of the injector body and has a hollow interior adapted for receiving the intraocular lens. The heater is integrated with the intraocular lens delivery system and is adapted to heat the intraocular lens.

29 Claims, 12 Drawing Sheets

(56) References Cited

U.S. PATENT DOCUMENTS

| | | |
|---|---|---|
| 5,944,725 A | 8/1999 | Cicenas et al. |
| 6,143,001 A | 11/2000 | Brown et al. |
| 6,193,683 B1 * | 2/2001 | Ludin et al. ............. 604/22 |
| 6,312,433 B1 | 11/2001 | Butts et al. |
| 6,355,046 B2 | 3/2002 | Kikuchi et al. |
| 6,387,101 B1 | 5/2002 | Butts et al. |
| 6,398,789 B1 | 6/2002 | Capetan |
| 6,447,519 B1 | 9/2002 | Brady et al. |
| 6,468,282 B2 | 10/2002 | Kikuchi et al. |
| 6,503,275 B1 | 1/2003 | Cumming |
| 6,506,195 B2 | 1/2003 | Chambers et al. |
| 6,558,395 B2 | 5/2003 | Hjertman et al. |
| 7,014,641 B2 | 3/2006 | Kobayashi et al. |
| 8,246,631 B2 | 8/2012 | Pynson |
| 2003/0033013 A1 * | 2/2003 | Callahan et al. ......... 623/6.21 |
| 2004/0024361 A1 | 2/2004 | Fago et al. |
| 2005/0283164 A1 | 12/2005 | Wu et al. |
| 2008/0097461 A1 | 4/2008 | Boukhny et al. |

FOREIGN PATENT DOCUMENTS

| | | |
|---|---|---|
| GB | 1274949 | 5/1972 |
| JP | 64015042 | 1/1989 |
| JP | 2000005204 | 1/2000 |
| JP | 2002516709 | 6/2002 |
| JP | 2006068441 | 3/2006 |
| RU | 1814870 | 5/1993 |
| RU | 2138232 | 9/1999 |
| RU | 2197204 | 1/2003 |
| WO | WO 01/39701 | 6/2001 |
| WO | WO 02/060338 A2 | 8/2002 |
| WO | WO 02/100468 | 12/2002 |
| WO | WO 2006/007303 | 1/2005 |

* cited by examiner

INTRAOCULAR LENS DELIVERY SYSTEM WITH TEMPERATURE CONTROL

FIELD OF THE INVENTION

The present invention relates to a device for delivering an intraocular lens into an eye and more particularly to a temperature-controlled intraocular lens delivery device.

BACKGROUND OF THE INVENTION

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. The IOL is placed in an IOL injector in a folded state. The tip of the IOL injector is inserted into the incision, and the lens is delivered into the eye.

Many IOLs manufactured today are made from a polymer with specific characteristics. These characteristics allow the lens to be folded, and when delivered into the eye, allow the lens to unfold into the proper shape. The polymers used to make these lenses have characteristics that are temperature-dependant. Heating the polymer allows the IOL to be compressed more easily, thus allowing it to fit through a smaller incision. A smaller incision is desirable because it promotes faster healing and is less traumatic for the patient.

The temperature characteristics of the polymers used to make IOLs can impact the lens implantation process significantly. For some polymers, a change in hardness or viscosity occurs over a relatively narrow range. For example, at colder temperatures, the polymer may become brittle and break if folded. At higher temperatures, the polymer may become gooey and lose its shape retaining ability. Therefore, it is desirable to maintain the polymer in a specific temperature range so that the IOL can maintain its integrity.

In practice, some surgeons have manually heated IOLs using the outside of autoclaves or warmers designed to warm baby wipes. Such warming is uncontrolled. As noted, the polymers used to manufacture artificial lenses are sensitive to temperature, and more precise temperature control can achieve desired results.

Therefore, a need exists for a temperate-controlled intraocular lens injection device.

SUMMARY OF THE INVENTION

In one embodiment consistent with the principles of the present invention, the present invention is an intraocular lens delivery system having an injector body, a plunger, a nozzle portion, and a heater. The plunger is slidably movable within the injector body. The nozzle portion is located on a distal end of the injector body and has a hollow interior adapted for receiving the intraocular lens. The heater is integrated with the intraocular lens delivery system and is adapted to heat the intraocular lens.

In another embodiment consistent with the principles of the present invention, the present invention is an intraocular lens delivery system including a hand piece, a cartridge, and a heater. The hand piece has a body and a plunger adapted to reciprocate in the body. The cartridge has a chamber in the cartridge and a nozzle on a distal end of the cartridge. The chamber is adapted to hold an intraocular lens. The nozzle has a hollow interior connected to the chamber. The cartridge is adapted to fit into the hand piece. The heater heats the intraocular lens.

In another embodiment consistent with the principles of the present invention, the present invention is a device for delivering an intraocular lens into an eye. The device has an injector body, a plunger, a nozzle portion, a heater, a power source, a controller, and an interface between the heater and the controller. The plunger is slidably movable within the injector body. The nozzle portion is located near a distal end of the injector body. The nozzle portion has a hollow interior capable of holding an intraocular lens. The heater is located near the intraocular lens and adapted to heat the intraocular lens. The power source provides power to the heater. The controller controls the operation of the heater. The controller is adapted to regulate the temperature of the intraocular lens.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
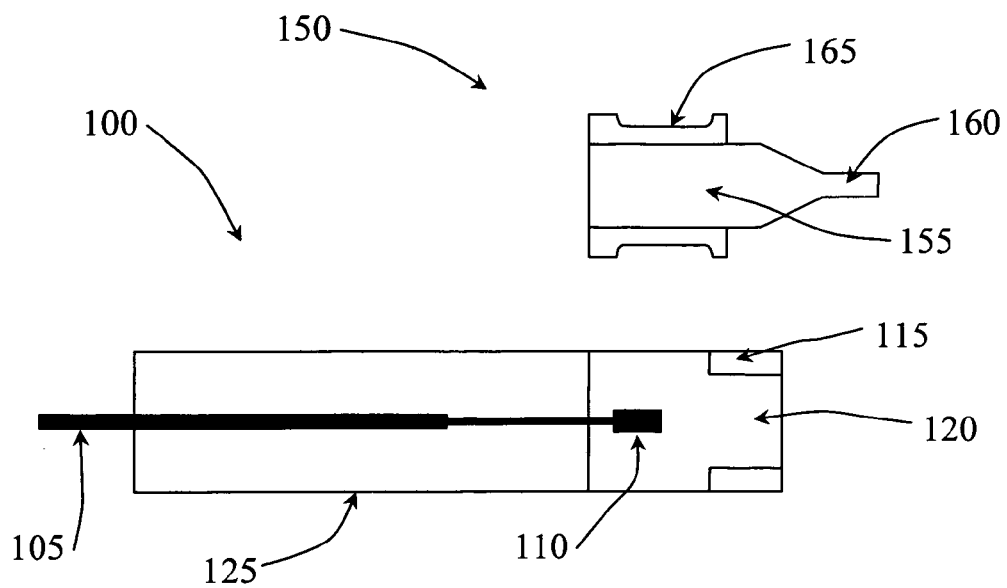
FIG. 1 is a top cross section view of a cartridge and hand piece that collectively function as an intraocular lens injector.

FIG. 1 is a top cross section view of a cartridge and hand piece that collectively function as an intraocular lens injector. In the embodiment pictured in FIG. 1, a two piece IOL injector system includes hand piece 100 and cartridge 150. In hand piece 100, injector body 125 houses a shaft 105 connected to a plunger 110. Shaft 105 is typically rigid and is connected to plunger 110 such that movement of shaft 105 translates into movement of plunger 110. In this manner, plunger 110 is designed to reciprocate within injector body 125. Two tabs, such as tab 115 are located on one end of hand piece 100. Area 120 is adapted to receive cartridge 150.

Cartridge 150 includes two tabs, such as tab 165, a nozzle 160, and a chamber 155. Chamber 155 holds an IOL. Nozzle 160 is hollow and is designed to allow an IOL to pass through it and into an eye. The interior of cartridge 150 contains a continuous passage that includes chamber 155 and nozzle 160. An IOL located in chamber 155 can be transferred out of cartridge through nozzle 160.

Figure 2:
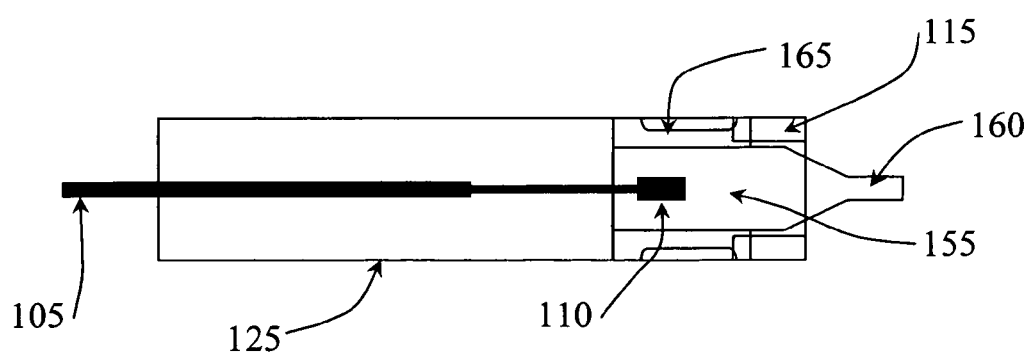
FIG. 2 is a top cross section view of a cartridge and hand piece that collectively function as an intraocular lens injector.

FIG. 2 shows how cartridge 150 and hand piece 100 fit together. As depicted in the embodiment shown in FIG. 2, cartridge 150 is located in area 120. Plunger 110 is designed to reciprocate within injector body 125 and chamber 155. Shaft 105 and plunger 110 are generally constrained to move back and forth in a direction that is parallel to body 125. The tabs on cartridge 150, such as tab 165, are designed to fit under the tabs on hand piece 100, such as tab 115. In this position, cartridge 150 is secured to hand piece 100.

In operation, shaft 105 is moved thus causing plunger 110 to move. To insert cartridge 150, shaft 105 and plunger 110 are drawn back so that plunger 110 is located outside of area 120. Area 120 receives cartridge 150, and plunger 110 is advanced into cartridge 150. In particular, plunger 110 is designed to enter chamber 155 and contact the IOL contained in chamber 155. When plunger 110 is advanced further, is pushes the IOL out of chamber 155 through nozzle 160. Nozzle 160 is inserted into an incision made in the cornea thus allowing the IOL to be delivered into the eye.

Figure 3:
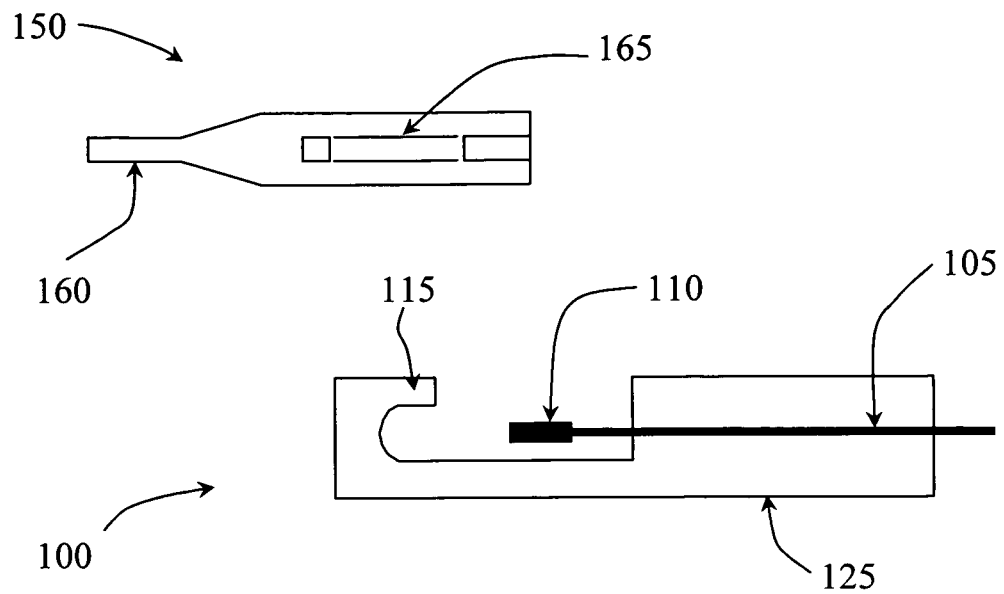
FIG. 3 is a side cross section view of a cartridge and hand piece that collectively function as an intraocular lens injector.
Figure 4:
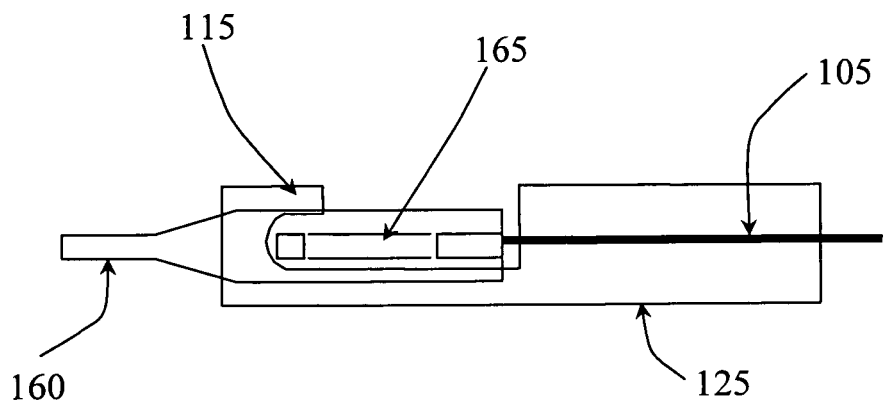
FIG. 4 is a side cross section view of a cartridge and hand piece that collectively function as an intraocular lens injector.

FIGS. 3 and 4 show a side cross section view of the cartridge 150 and hand piece 100 depicted in FIGS. 1 and 2. In this embodiment, cartridge 150 fits into hand piece 100 as shown. In FIG. 4, plunger 110 is in chamber 155 of cartridge 150.

Figure 5:
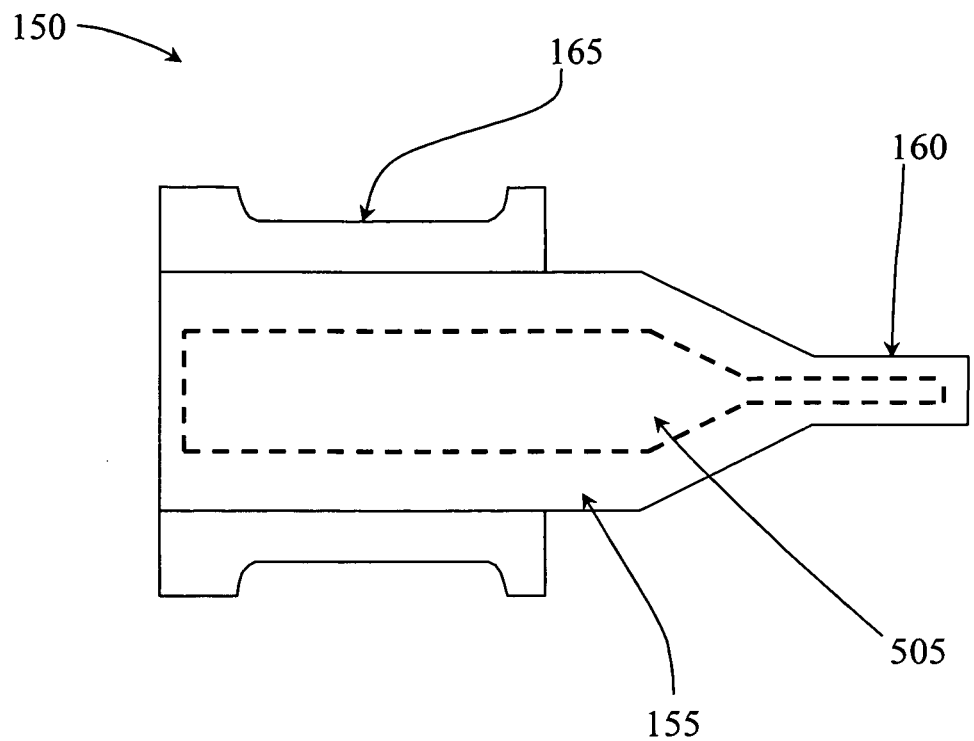
FIG. 5 is an exploded top cross section view of a cartridge with a heater according to an embodiment of the present invention.
Figure 6:
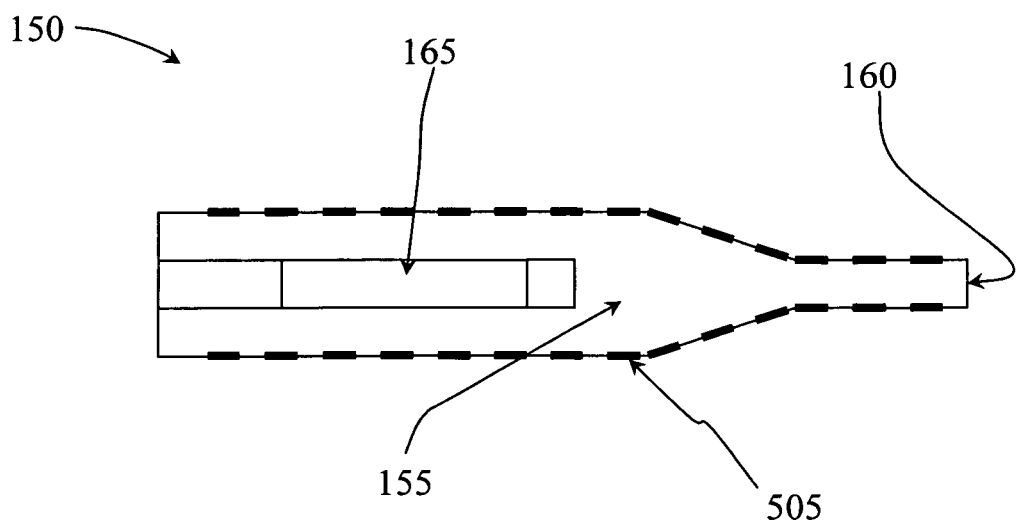
FIG. 6 is an exploded side cross section view of a cartridge with a heater according to an embodiment of the present invention.

FIGS. 5 and 6 depict exploded cross section views (both top and side) of a cartridge with a heater according to an embodiment of the present invention. The location of heater 505 is shown by the dashed lines. In the embodiment of FIGS. 5 and 6, heater 505 is located above and below chamber 155. This allows heater 505 to heat the IOL contained in chamber 155. In addition, heater 505 extends to nozzle 160, allowing heat to be transferred to the IOL while the IOL is in the nozzle 160. Heater 505 may also be located such that it surrounds chamber 155 or such that it is only on one side of chamber 155.

Heater 505 is typically a resistive type heater. In one embodiment, heater 505 is a continuous wire with a resistance through which a current is passed. In other embodiments, heater 505 contains resistive elements connected in series through which a current is passed. The amount of current passed through heater 505 and the resistive characteristics of heater 505 are selected to provide the proper amount of heat for heating an IOL contained in chamber 155.

Electrical connections (not shown) provide current to heater 505. These connections typically provide current to heater 505 from a power source, such as a battery. In addition, a control line (not shown) provides signals that control the operation of heater 505. In this embodiment, a controller (not shown) receives temperature information from heater 505 and provides signals that control the operation of heater 505.

Heater 505 may be located on the outer surface of cartridge 150, the inner surface of cartridge 150, or embedded in cartridge 150. Typically, cartridge 150 is made from a polymeric material. Heater 505 may be embedded in the polymeric material.

Figure 7:
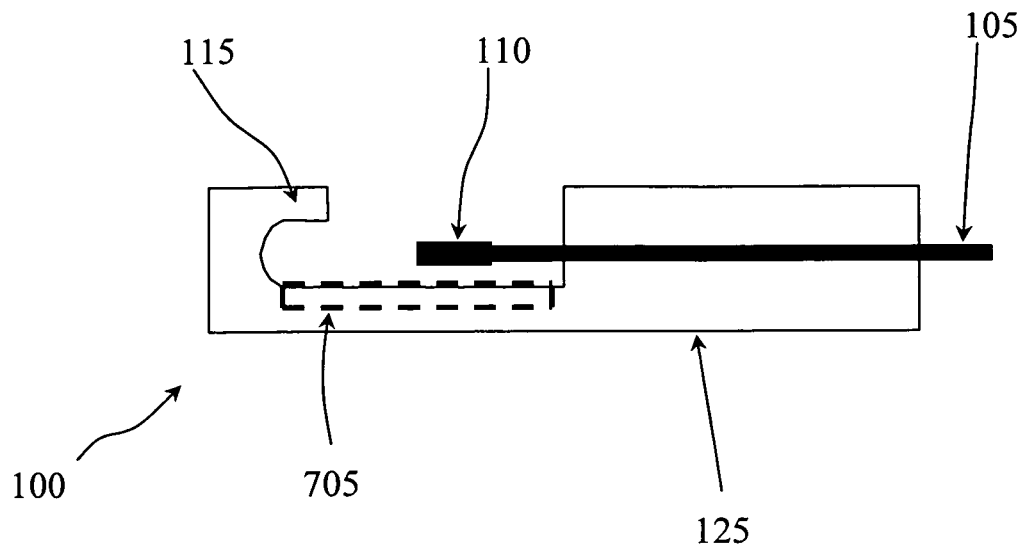
FIG. 7 is an exploded side cross section view of a hand piece with a heater located on the hand piece body according to an embodiment of the present invention.
Figure 8:
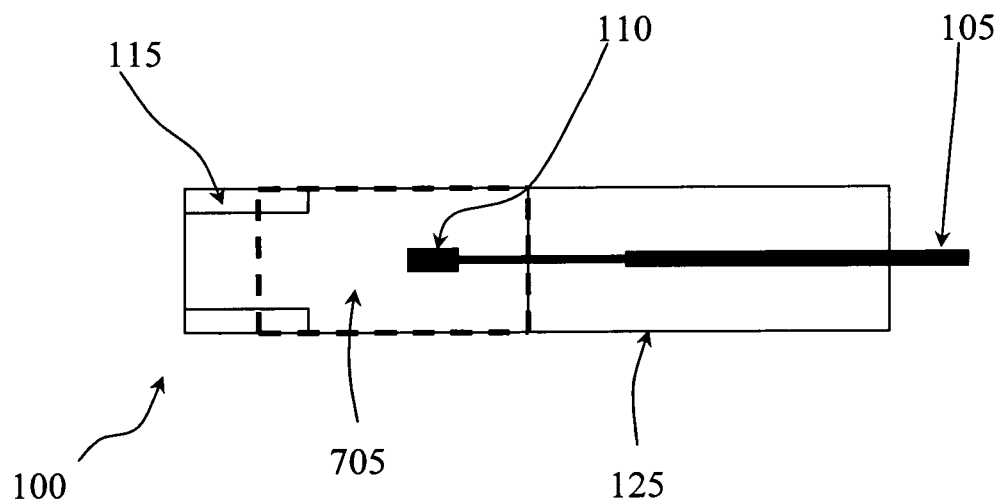
FIG. 8 is an exploded top cross section view of a hand piece with a heater located on the hand piece body according to an embodiment of the present invention.

FIGS. 7 and 8 depict exploded cross section views (both top and side) of a hand piece with a heater according to an embodiment of the present invention. The location of heater 705 is shown by the dashed lines. In this embodiment, heater 705 is located below plunger 110. In this manner, cartridge 150 fits in hand piece 100 above heater 705. Heater 705 heats cartridge 150 and the IOL that it contains. Like heater 505, heater 705 is a resistive type heater.

Heater 705 may be located on the outer surface of hand piece 100, the inner surface of hand piece 100, or embedded in hand piece 100. When hand piece 100 is made of a polymeric material, heater 705 may be embedded in the polymeric material. When hand piece 100 is made of a metallic material, heater 705 may be located on one of its surfaces.

Electrical connections (not shown) provide current to heater 705. These connections typically provide current to heater 705 from a power source, such as a battery. In addition, a control line (not shown) provides signals that control the operation of heater 705. In this embodiment, a controller (not shown) receives temperature information from heater 705 and provides signals that control the operation of heater 705.

Figure 9:
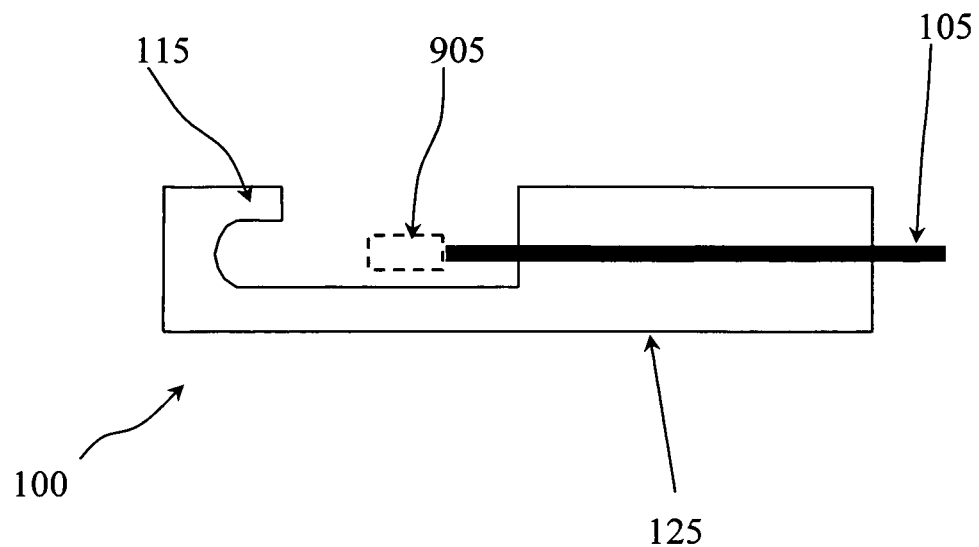
FIG. 9 is an exploded side cross section view of a hand piece with a heater located on the plunger according to an embodiment of the present invention.
Figure 10:
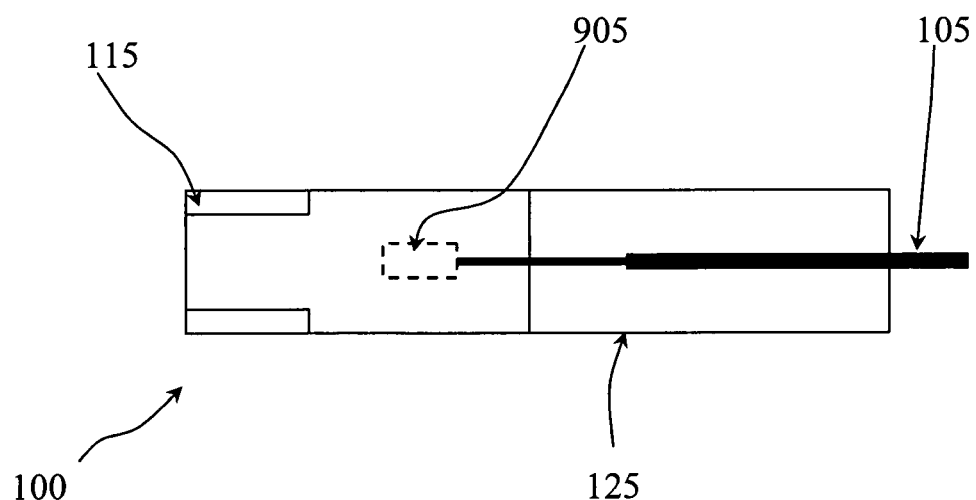
FIG. 10 is an exploded top cross section view of a hand piece with a heater located on the plunger according to an embodiment of the present invention.

FIGS. 9 and 10 depict exploded cross section views (both top and side) of a hand piece with a heater according to an embodiment of the present invention. The location of heater 905 is shown by the dashed lines. In this embodiment, the heater is located on the plunger 110. Heat from heater 905 is transferred to the IOL directly when the plunger 110 is inserted into chamber 155 of cartridge 150. Like heaters 505 and 705, heater 905 is a resistive type heater.

Heater 905 may be located on the outer surface of plunger 110, the inner surface of plunger 110, or embedded in plunger 110. When plunger 110 is made of a polymeric material, heater 705 may be embedded in the polymeric material.

Electrical connections (not shown) provide current to heater 905. These connections typically provide current to heater 905 from a power source, such as a battery. In addition, a control line (not shown) provides signals that control the operation of heater 905. In this embodiment, a controller (not shown) receives temperature information from heater 905 and provides signals that control the operation of heater 905.

In one embodiment, only one of the above heater configurations is selected. In other words, if a heater is located in the cartridge, then it is not present in the hand piece. Likewise, if a heater is present in the hand piece, it is not present in the cartridge.

In another embodiment, two heaters may be used. For example, a heater may be present on the plunger 110 as well as on the injector body 125. This allows heat to be transferred to the IOL indirectly through the cartridge (in the case of the heater located on the injector body 125) as well as directly (in the case of the heater located on the plunger 110). Numerous other similar configurations are within the scope of the present invention.

The operation of heaters 505, 705, and 905 is similar. Each of these heaters produces heat when current is passed through them. Typically, a controller controls the amount of current and timing of the current applied to the heaters. When actuated, the heaters are designed to maintain the IOL within a desired temperature range.

Figure 11:
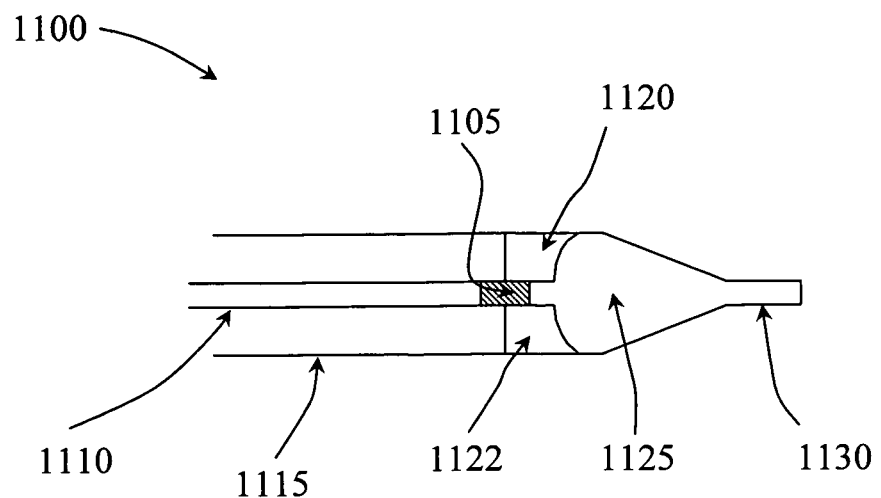
FIG. 11 is a top cross section view of an intraocular lens injector according to an embodiment of the present invention.
Figure 12:
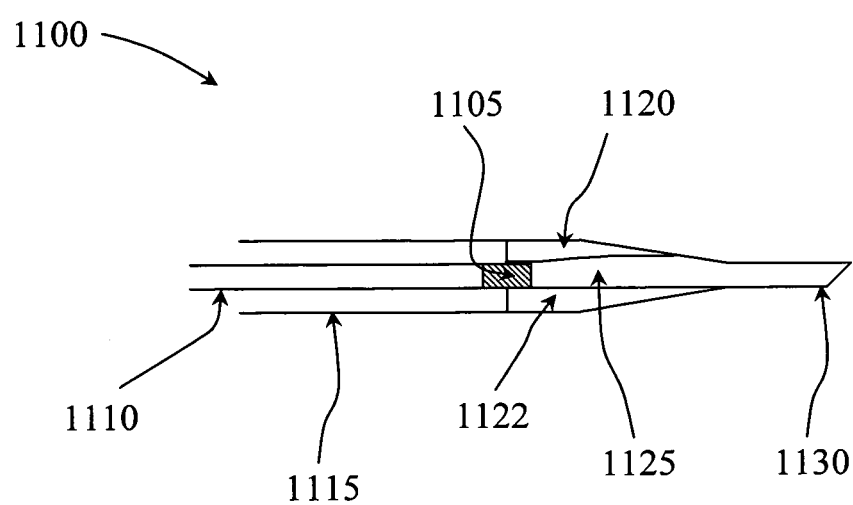
FIG. 12 is a side cross section view of an intraocular lens injector according to an embodiment of the present invention.

FIGS. 11 and 12 depict top and side cross section views of an IOL injector into which a heater may be incorporated. In the embodiment of FIG. 11, an IOL delivery system 1100 includes a plunger 1105 located on one end of a shaft 1110. Shaft 1110 is typically rigid and is connected to plunger 1105 such that movement of shaft 1110 translates into movement of plunger 1105. In this manner, plunger 1105 is designed to reciprocate within injector body 125. Guides 1120, 1122 ensure that plunger 1105 moves back and forth in a direction parallel to housing 1115. Housing 1115 contains plunger 1105 and shaft 1110.

Nozzle portion 1130 is located on one end of IOL delivery system 1100. Hollow interior 1125 is located in nozzle portion 1130 and is designed to hold an IOL. A continuous passage extends from guides 1120, 1122 through hollow interior 1125 and out of nozzle portion 1130 at its distal end. An IOL contained in hollow interior 1125 adjacent to guides 1120, 1122 can pass out of the distal or tip end of nozzle portion 1130 and into an eye.

In operation, shaft 1110 is moved thus causing plunger 1105 to move. Shaft 1110 and plunger 1105 are generally constrained to move back and forth in a direction that is parallel to and within housing 1115. An IOL is located in hollow interior 1125 adjacent to guides 1120, 1122. Plunger 1105 is designed to engage the IOL and push the IOL through hollow interior 1125, out of the distal or tip end of nozzle portion 1130 and into an eye. The distal or tip end of nozzle portion 1130 in inserted into an incision made in the cornea. The IOL is delivered into the eye through this incision.

Figure 13:
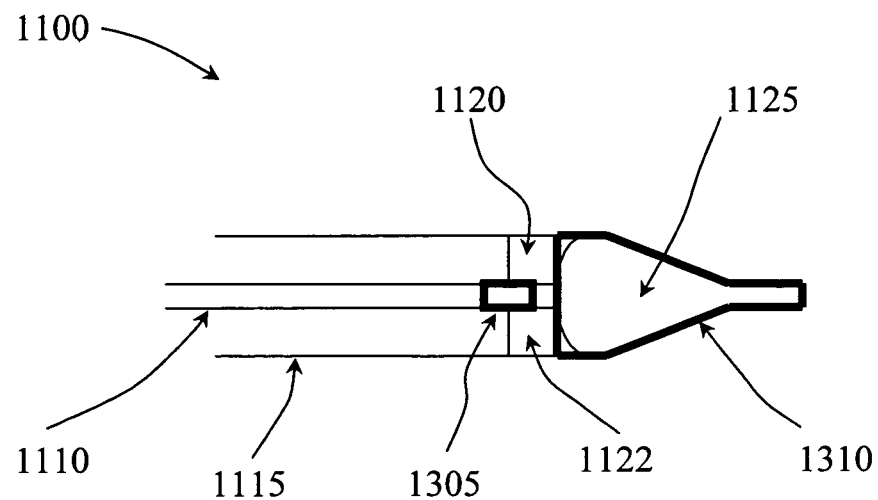
FIG. 13 is a top cross section view of an intraocular lens injector depicting two different heater locations according to an embodiment of the present invention.
Figure 14:
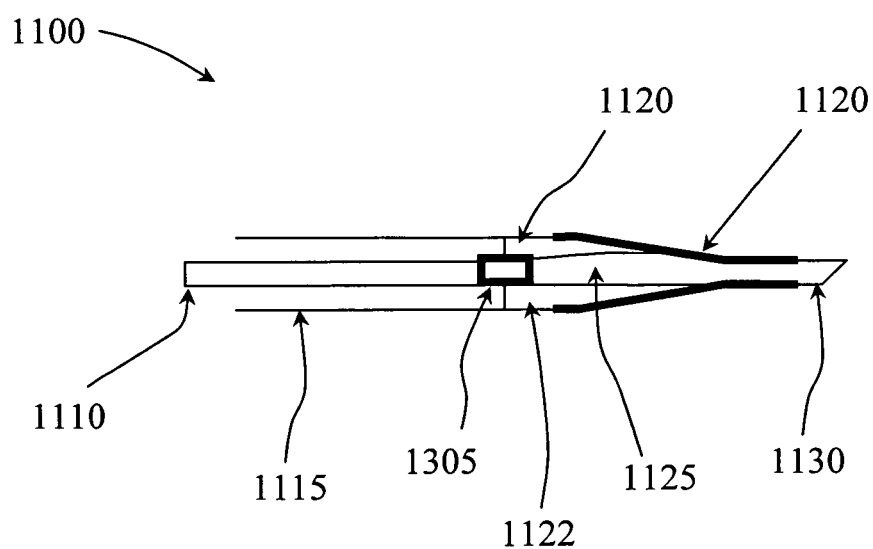
FIG. 14 is a side cross section view of an intraocular lens injector depicting two different heater locations according to an embodiment of the present invention.

FIGS. 13 and 14 show top and side cross section views of an intraocular lens injector with two different heater locations according to an embodiment of the present invention. In FIGS. 13 and 14, heater 1305 is located on the plunger, and heater 1310 is located on the nozzle portion. The location of heaters 1305, 1310 is shown by the solid lines. In the embodiment of FIGS. 13 and 14, heater 1305 is located on the plunger, and heater 1310 is located above and below the hollow interior 1125 of the nozzle portion 1130. In other embodiments, heater 1310 surrounds hollow interior 1125 or is located on one side of it.

When heater 1305 is located on plunger 1105, heat is transferred to the IOL when plunger 1105 makes contact with the IOL. When heater 1310 is located on nozzle portion 1130 and surrounds hollow interior 1125, heat is transferred to the IOL as it resides in hollow interior 1125.

Heaters 1305, 1310 are typically resistive type heaters. In one embodiment, heaters 1305, 1310 each comprise a continuous wire with a resistance through which a current is passed. In other embodiments, heaters 1305, 1310 each contain resistive elements connected in series through which a current is passed. The amount of current passed through heaters 1305, 1310 and the resistive characteristics of heaters 1305, 1310 are selected to provide the proper amount of heat for heating an IOL.

Electrical connections (not shown) provide current to heaters 1305, 1310. These connections typically provide current to heaters 1305, 1310 from a power source, such as a battery. In addition, a control line (not shown) provides signals that control the operation of heaters 1305, 1310. In this embodiment, a controller (not shown) receives temperature information from heaters 1305, 1310 and provides signals that control the operation of heaters 1305, 1310.

Heater 1305 may be located on the outer surface of plunger 1105, the inner surface of plunger 1105, or embedded in plunger 1105. Typically, plunger 1105 is made from a polymeric material. In such a case, heater 1105 may be embedded in the polymeric material. Likewise, heater 1310 may be located on the outer surface of nozzle portion 1130, the inner surface of nozzle portion 1130, or embedded in nozzle portion 1130. Typically, nozzle portion 1130 is made from a polymeric material. In such a case, nozzle portion 1130 may be embedded in the polymeric material.

In one embodiment, only one of the above heater configurations is selected. In other words, if a heater is located in the plunger 1105, then it is not present in the nozzle portion 1130. Likewise, if a heater is present in the nozzle portion 1130, it is not present in the plunger 1105.

In another embodiment, two heaters may be used. For example, a heater may be present on the plunger 1105 as well as on the nozzle portion 1130. This allows heat to be transferred to the IOL indirectly through nozzle portion 1130 (in the case of the heater located on the nozzle portion 1130) as well as directly (in the case of the heater located on the plunger 1105). Numerous other similar configurations are within the scope of the present invention.

The operation of heaters 1305 and 1310 is similar. Each of these heaters produces heat when current is passed through them. Typically, a controller controls the amount of current and timing of the current applied to the heaters. When actuated, the heaters are designed to maintain the IOL within a desired temperature range.

As shown in the above embodiments, a heater can be located in close proximity to an IOL to heat the IOL so that it can be more easily delivered into the eye. Since IOLs are generally made or a polymeric material that is temperature sensitive, providing heat through an integral heater helps to keep the IOL at a temperature at which it can be more easily compressed while still maintaining its shape characteristics. Thus, a heater can be used to maintain the IOL within a desired temperature range so that the IOL can be more easily delivered into the eye.

Figure 15:
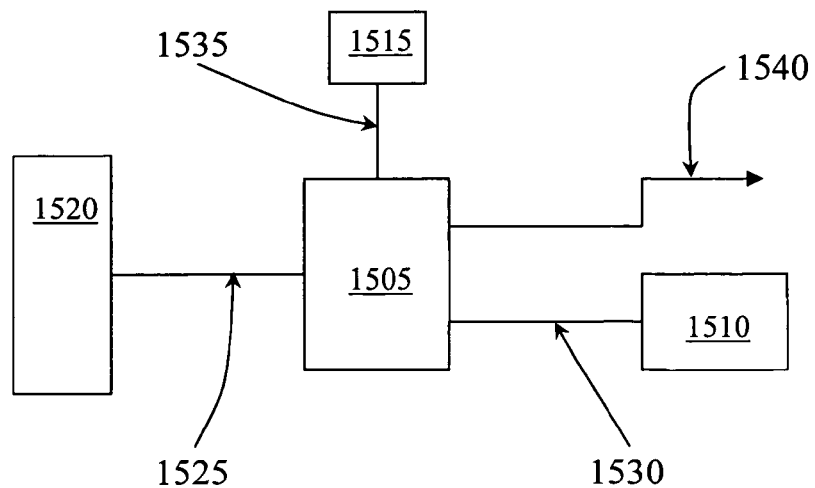
FIG. 15 is a block diagram of a portion of an intraocular lens injector system according to an embodiment of the present invention.

While the above embodiments detail the location and composition of the heater, the following embodiments describe the IOL delivery system more completely. FIG. 15 is a block diagram of a portion of an intraocular lens injector system according to an embodiment of the present invention. In the embodiment of FIG. 15, one part of the IOL delivery system includes a controller 1505, a motor, 1510, an input device 1515, and a power source 1520. Controller 1505 is connected to motor 1510 via interface 1530, to input device 1515 via interface 1535, and to power source 1520 via interface 1525. Interface 1540 connects controller 1505 to a heater (not shown).

Controller 1505 is typically an integrated circuit capable of performing logic functions. In various embodiments, controller 1505 is a motor controller or a heater controller. In other embodiments, controller 1505 is a simple microprocessor. Controller 1505 is typically in the form of a standard IC package with power, input, and output pins.

In the embodiment of FIG. 15, controller 1505 is an integrated circuit capable of receiving an input from input device 1515 via interface 1535. Controller receives its power from power source 1520 via interface 1525. Controller 1505 may also receive information from a heater (not shown) via interface 1540. In this embodiment, controller 1505 has two control outputs. Controller 1505 sends control outputs to motor 1510 via interface 1530. Controller also sends control outputs to a heater (not shown) via interface 1540.

Input device 1515 is typically a switch or a button that activates some part of the IOL delivery system. In one embodiment, input device 1515 is a switch that is activated to activate the heater.

Power source 1520 provides power to controller 1505, motor 1510, and heater (not shown). In one embodiment, power source 1520 is a battery. In another embodiment, power source 1520 is a cable that directs power from a surgical console.

Motor 1510 is designed to drive a plunger to inject the IOL into an eye. In one embodiment, motor 1510 is a stepper motor. Interfaces 1525, 1530, 1535, and 1540 can be any type of interface suitable. In one embodiment, these interfaces are wires. In other embodiments, these interfaces are capable of sending and receiving power and/or data.

Figure 16:
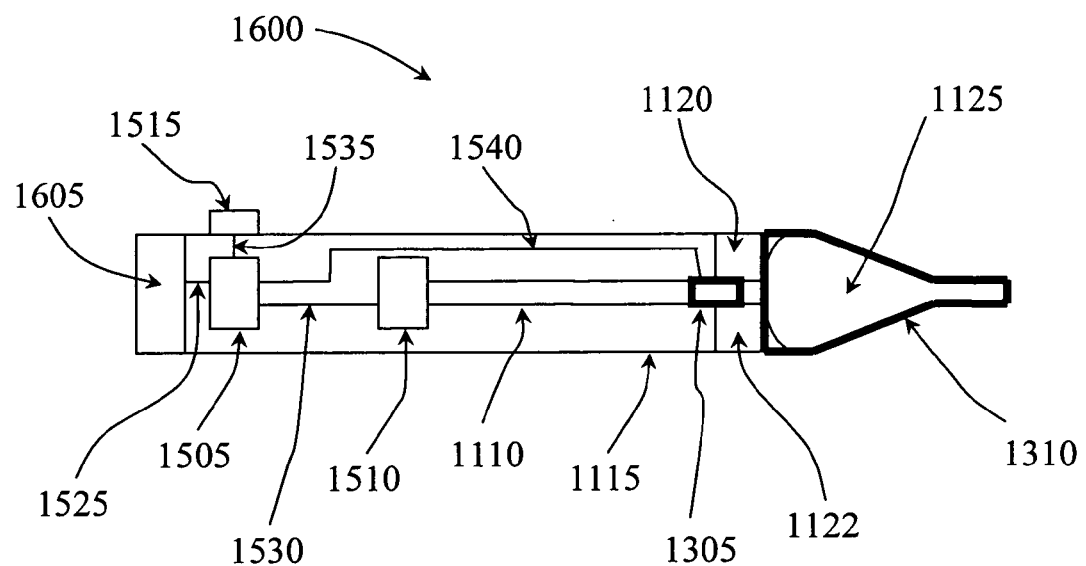
FIG. 16 is a top cross section view of a battery-powered intraocular lens delivery system depicting two different heater locations according to an embodiment of the present invention.

FIG. 16 is a top cross section view of a battery-powered intraocular lens delivery system depicting two different heater locations according to an embodiment of the present invention. The IOL delivery system 1600 of FIG. 16 joins the elements of FIGS. 13 and 14 with the elements of FIG. 15. In FIG. 16, IOL delivery system 1600 includes battery 1605, controller 1505, input device 1515, motor 1510, shaft 1110, housing 1115, guides 1120, 1122, hollow interior 1125, interfaces 1525, 1530, 1535, 1540, and heaters 1305, 1310. An indicator, such as an LED, (not shown) may also be present on housing 1115.

Battery 1605 is located within housing 1115 at one end of IOL delivery system 1600. Battery 1605 provides power to controller through interface 1525. Battery 1605 also provides power to motor 1510 and one or both heaters 1305, 1310. Input device 1515, when activated, provides a signal to controller 1505 through interface 1535. Controller 1505 controls heater 1305, 1310 through signals sent over interface 1540. While interface 1540 is shown as connecting heater 1305 to controller 1505, it may connect heater 1310 to controller 1505. Controller 1505 controls the operation of motor 1510 through signals sent over interface 1530. Motor 1510 is connected to shaft 1110 and moves shaft 1110 when activated. Shaft 1110 is connected to a plunger (not shown). Guides 1120, 1122, located in housing 1115, constrain shaft 1110 and plunger (not shown) to move back and forth in a direction that is generally parallel to housing 1115. Hollow interior 1125 is located in the nozzle portion of the IOL delivery system 1600. Two heater locations 1305, 1310 are also depicted.

While two heater locations are shown, either one or both of the heaters 1305, 1310 may be present. In one embodiment, heater 1305 is present and heater 1310 is not. In such a case, heater 1305, located on the plunger, heats an IOL directly when it contacts or comes near the IOL. In another embodiment, heater 1310 is present and heater 1305 is not. In such a case, heater 1310 heats the IOL. In yet another embodiment, both heaters 1305 and 1310 are present. In this case, both heaters heat the IOL.

In operation, controller 1505 receives an input from input device 1515. As noted, input device 1515 is typically a switch or button. In this example, the input received directs the controller 1505 to turn on a heater, such as heater 1305 or heater 1310, or both. Via interface 1540, controller 1505 switches the heater on so that it can heat the IOL. Controller 1505 also receives temperature information from heater 1305 and/or heater 1310 over interface 1540. Controller 1505 controls heater 1305 and/or heater 1310 to maintain the IOL within a desired temperature range. An indicator, such as a light emitting diode, (not shown), illuminates to provide an indication that the IOL is in the desired temperature range. While the IOL is in the desired temperature range, controller activates motor 1510 to drive shaft 1110 and a plunger (co-located with heater 1305) to deliver an IOL out of hollow interior 1125 and into the eye.

Controller 1505 can utilize any number of different algorithms to control heater 1305 and/or heater 1310. In one embodiment consistent with the principles of the present invention, controller 1505 uses an on/off control algorithm to switch the heater on and off to maintain the IOL within a desired temperature range. In another embodiment, controller 1505 controls the amount of current applied to heater 1305 and/or heater 1310 to regulate its temperature. In this method, the heater is maintained in a temperature range to ensure that the IOL is maintained in a desired temperature range.

In another embodiment, controller 1505 implements a proportional-integral-derivative controller ("PID controller"). A PID controller accepts a feedback signal from the heater and controls the heater by using the feedback signal. A PID controller can effectively maintain the heater at a desired set point. For example, if the set point is 35 or 40 degrees Celsius, then the PID controller maintains the heater at 35 or 40 degrees Celsius. The heater can be maintained at any set point by using a PID controller.

The desired temperature range can be preset at the factory. Since the IOL delivery system is used to deliver IOLs made of the same polymeric material, a preset temperature range of a few degrees Celsius or less is appropriate for the desired temperature range. Typically, the polymeric material used to make IOLs has temperature dependent characteristics that are observable over relatively small temperature ranges of a few degrees Celsius. In such a case, a desired temperature range should be in the range of a few degrees Celsius or less.

Controller 1505 can utilize any number of different algorithms to control motor 1510. In the case where motor 1510 is a stepper motor, controller 1505 advances the motor's shaft incrementally, thus advancing the shaft 1110 and plunger incrementally. In one embodiment shaft 1110 is the shaft found on a stepper motor. In another embodiment, the shaft on a stepper motor is coupled to shaft 1110.

Figure 17:
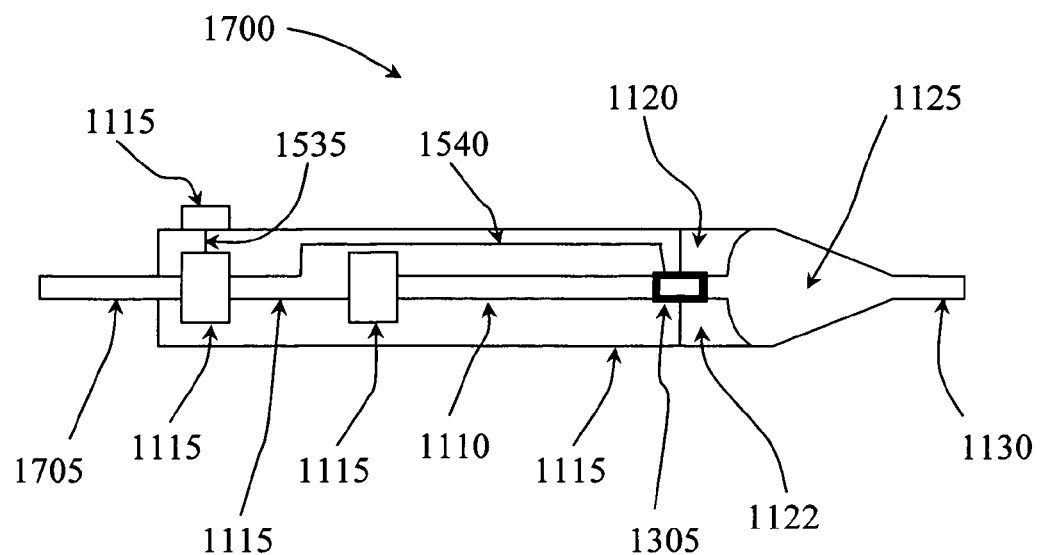
FIG. 17 is a top cross section view of an intraocular lens delivery system with a heater located on the plunger according to an embodiment of the present invention.

The embodiment of FIG. 17 is the same as that of FIG. 16 except that power is provided to the IOL delivery system 1700 through a cable 1705. Cable 1705 extends from the IOL delivery system 1700 to a surgical console (not shown). The surgical console typically contains a number of ports, such as ports that provide electric or pneumatic power. The console also contains a display that displays information about the operation of the system. In the embodiment shown in FIG. 17, controller 1505 interfaces with cable 1705. Controller 1505 may send information to and receive information from the console via cable 1705. In one embodiment, the console performs most, if not all, of the control functions. In such a case, controller 1505 may not be present. Instead, cable 1705 carries interfaces 1530, 1535, and 1540, receives input signals from input device 1515, and provides control signals to motor 1510 and heater 1305.

In FIG. 17, only one heater, heater 1305, is shown. Heater 1305 is located on the plunger and is designed to directly heat the IOL. Nozzle portion 1130 is also visible.

Figure 18:
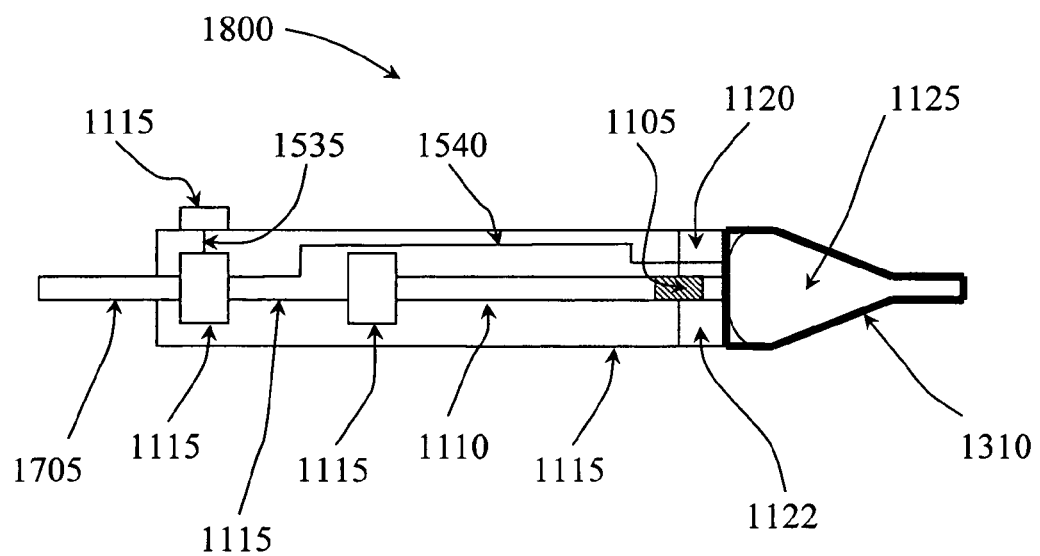
FIG. 18 is a top cross section view of an intraocular lens delivery system with a heater located on the nozzle according to an embodiment of the present invention.

The embodiment of FIG. 18 is the same as that of FIG. 17 except that the heater 1310 is located on the nozzle portion 1130 and not on the plunger 1105.

In operation, IOL delivery system 1700 and IOL delivery system 1800 each receive their power via cable 1705. Both operate in a similar fashion. In one embodiment, controller 1505 of IOL delivery system 1700 receives an input signal from input device 1515. This input signal tells the controller to activate heater 1305. Alternatively, when controller 1505 is not present and the control functions are handled by the surgical console, the input signal from input device 1515 is received by the console via cable 1705. Controller 1505, if present, or the console, if controller 1505 is not present, controls the operation of heater 1305 to maintain the IOL within a desired temperature range. While the IOL is in the desired temperature range, the surgeon inserts the tip end of nozzle portion 1130 into a small incision in the cornea of the eye and activates the plunger to inject the IOL into the eye. Typically, the surgeon depresses a foot switch to actuate motor 1510. Motor 1510 drives shaft 1110 and plunger 1105 displacing the IOL out of hollow interior 1125, through the tip end of nozzle portion 1130, and into the eye.

The foot switch is connected to the main surgical console. In this manner, the signal from the foot switch tells the console that the surgeon wishes to inject the IOL into the eye. The console either controls this operation directly by activating motor 1510 or it sends a signal to controller 1505, if present, and controller 1505 controls the operation of the motor. In this manner, if controller 1505 is not present, then the main surgical console controls the operation the IOL delivery device 1700.

Figure 19:
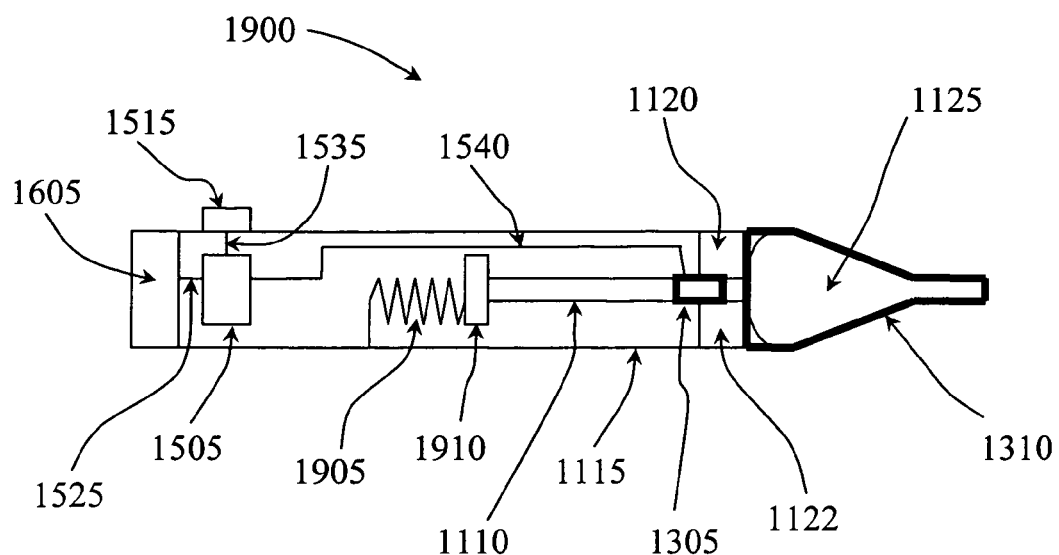
FIG. 19 is a top cross section view of a spring-actuated intraocular lens delivery system depicting two different heater locations according to an embodiment of the present invention.

The embodiment of FIG. 19 is the same as that of FIG. 16 except that spring 1905 and spring lock 1910 replace motor 1510. In this embodiment, spring 1905 provides the force to drive shaft 1110 and plunger 1105 to deliver the IOL into the eye. One end of spring 1905 is connected to housing 1115 or some structure (not shown) on the interior of housing 1115. Shaft lock 1910 acts to hold shaft 1110 in place. In this position, spring 1905 is under tension. When shaft lock 1910 is released, spring 1905 pushes shaft 1110 in a direction toward the end of nozzle portion 1130. This in turn pushes plunger 1105 and drives the IOL out of nozzle portion 1130 and into the eye.

In one embodiment, shaft lock 1910 is controlled by controller 1505. In another embodiment, shaft lock 1910 is held in place by a mechanical coupling (not shown) that is released by button or switch (not shown). In such a case, controller 1505 may be a simple controller designed to operate heater 1305 and/or heater 1310. In this case, the IOL delivery device 1900 may be disposable.

In operation, disposable IOL delivery device 1900 is activated by activating input device 1515. Input device 1515 is typically a switch or a button that turns on heater 1305, heater 1310, or both heaters 1305 and 1310. The heater(s) get their power from battery 1605. Battery 1605 supplies current to the heater(s). After the heater(s) warm the IOL so that the IOL is within a desired temperature range, an indicator (not shown) such as an LED is illuminated. This lets the surgeon know that the IOL is ready to be injected. The surgeon then inserts the tip end of the nozzle portion 1130 (which is located at heater 1310) into an incision in the cornea and releases the shaft lock 1910. The shaft lock may be disabled or released by activating a mechanical shaft lock release (not shown). Such a shaft lock release may be in the form of a switch or button. Once the shaft lock is released, the spring pushes shaft 1110 and plunger 1105 (which is located at heater 1305) toward the tip end of nozzle portion 1130. Plunger 1105 pushes the IOL out of interior cavity 1125, through the tip end of nozzle portion 1130, and into the eye.

Regardless of which embodiment is practiced, a safety feature may be added to the IOL delivery system. This safety feature allows the IOL to be inserted into the eye only when the IOL is within the desired temperature range. In such a case, the delivery of the IOL into the eye is prevented by a mechanical lock or by the controller (depending on the implementation) until the IOL reaches the desired temperature range. Such a safety scheme is easily implemented in the controller 1505 or the main surgical console.

Figure 20:
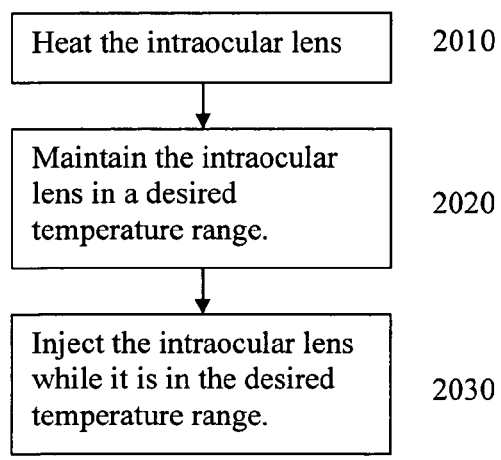
FIG. 20 is a flow chart of one method of operation of an intraocular lens injector system according to an embodiment of the present invention.

FIG. 20 is a flow chart of one method of operation of an intraocular lens injector system according to an embodiment of the present invention. In 2010, the IOL is heated. In 2020, the IOL is maintained within a desired temperature range. In 2030, the IOL is delivered into the eye while it is in the desired temperature range.

Figure 21:
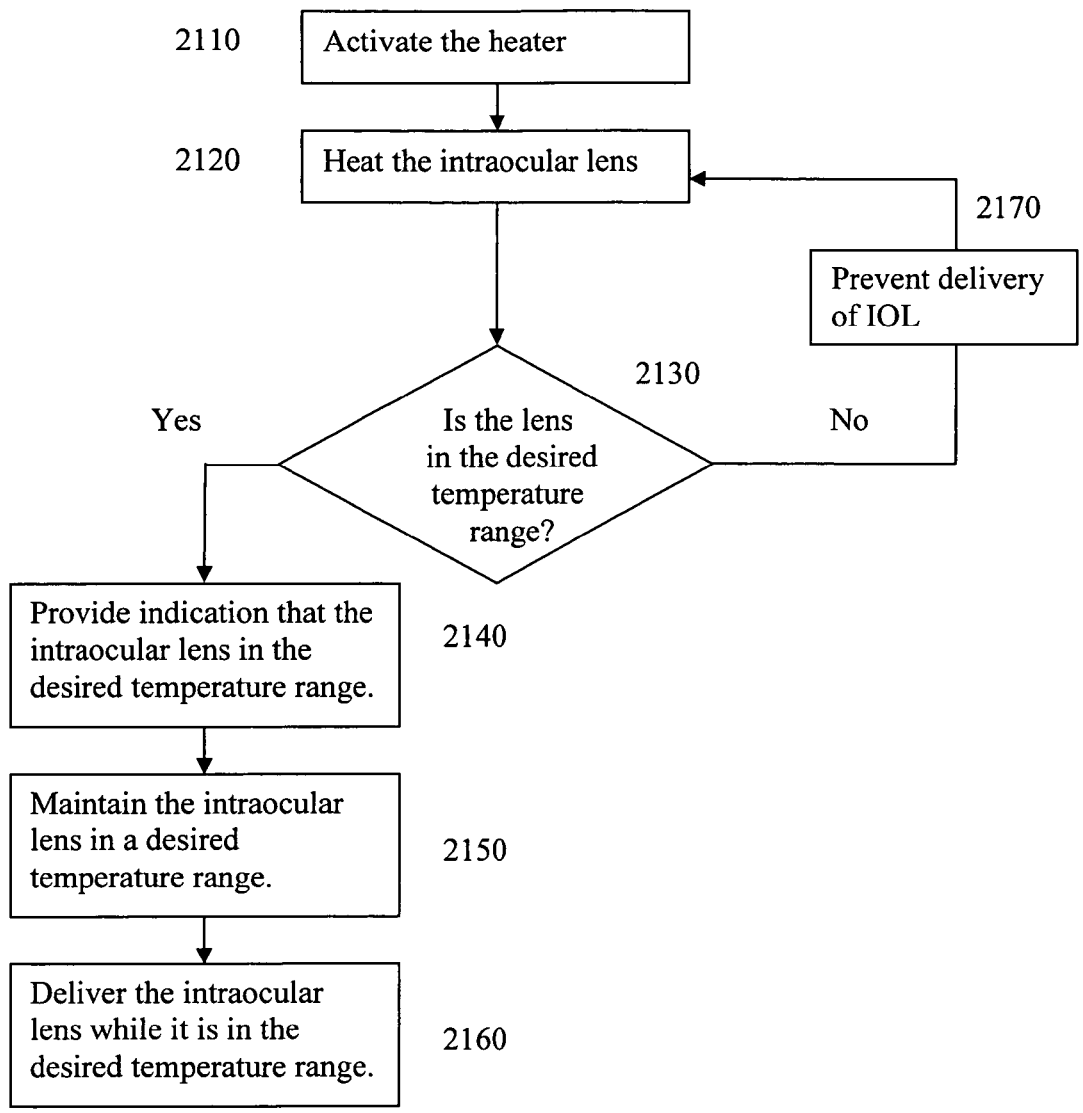
FIG. 21 is a flow chart of one method of operation of an intraocular lens injector system according to an embodiment of the present invention.

FIG. 21 is a flow chart of another method of operation of an intraocular lens injector system according to an embodiment of the present invention. In 2110 the heater is activated.

In 2120, the IOL is heated. If the IOL has not reached the desired temperature range in 2130, then the delivery of the IOL is prevented in 2170 and the IOL continues to be heated in 2120. If the IOL has reached the desired temperature range in 2130, then in 2140, an indication is provided that the IOL is in the desired temperature range. This indication can be visual such as illuminating an LED. In 2150, the temperature of the IOL is maintained in the desired temperature range. In 2160, the IOL is delivered into the eye while it is in the desired temperature range.

Figure 22:
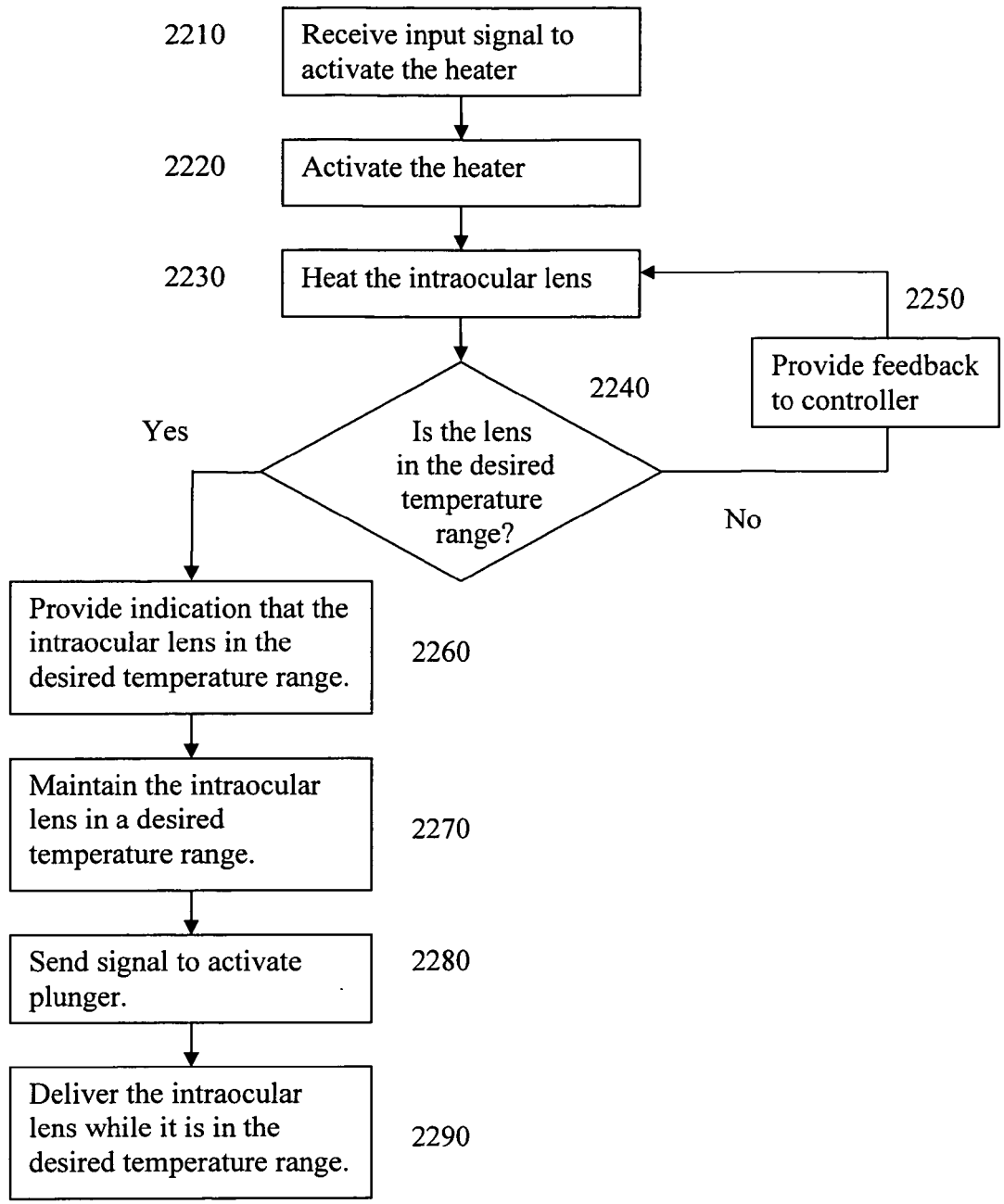
FIG. 22 is a flow chart of one method of operation of an intraocular lens injector system according to an embodiment of the present invention.

FIG. 22 is a flow chart of another method of operation of an intraocular lens injector system according to an embodiment of the present invention. In 2210, an input signal indicating that the heater should be activated is received. In 2220, the heater is activated. In 2230, the IOL is heated. If the IOL has not reached the desired temperature range in 2240, then in 2250, feedback is provided to the controller and in 2230, the IOL continues to be heated. If the IOL has reached the desired temperature range in 2240, then in 2260, an indication is provided that the IOL is in the desired temperature range. In 2270, the temperature of the IOL is maintained in the desired temperature range. In 2280, a signal is sent to activate the plunger. In 2290, the IOL is delivered into the eye while it is in the desired temperature range.

From the above, it may be appreciated that the present invention provides an improved system for delivering an intraocular lens into an eye. The present invention provides a temperature-controlled intraocular lens injection device that allows the lens to be heated to a desired temperature range thus improving its compressability. This allows the lens to be delivered through a smaller incision. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An intraocular lens delivery system comprising:
   an injector body;
   a plunger slidably movable within the injector body;
   a nozzle portion on a distal end of the injector body, the nozzle portion having a hollow interior adapted for receiving an intraocular lens;
   a heater integrated with the intraocular lens delivery system adapted to heat the intraocular lens while the intraocular lens is external to an eye; and
   an indicator on the injector body operable to be illuminated to display a visible indication to deliver the intraocular lens into the eye while the intraocular lens is external to the eye when the heater has heated the intraocular lens to a predetermined temperature range.

2. The intraocular lens delivery system of claim 1 wherein the heater is located on the nozzle portion.

3. The intraocular lens delivery system of claim 1 wherein the nozzle portion is made of a polymer and the heater is molded into the polymer.

4. The intraocular lens delivery system of claim 1 wherein the heater is located on the plunger.

5. The intraocular lens delivery system of claim 1 wherein the plunger is made of a polymer and the heater is molded into the polymer.

6. The intraocular lens delivery system of claim 1 further comprising a power source for providing power to the heater.

7. The intraocular lens delivery system of claim 6 wherein the power source is a battery.

8. The intraocular lens delivery system of claim 1 further comprising a controller for regulating the temperature of the intraocular lens.

9. The intraocular lens delivery system of claim 8 further comprising an interface between the heater and the controller.

10. The intraocular lens delivery system of claim 9 wherein the interface provides feedback to the controller so that the controller can operate the heater to maintain the intraocular lens within a desired temperature range.

11. The intraocular lens delivery system of claim 1 further comprising a motor for moving the plunger.

12. The intraocular lens delivery system of claim 1 further comprising a spring for moving the plunger.

13. The intraocular lens delivery system of claim 1 further comprising a switch for activating the heater.

14. An intraocular lens delivery system comprising:
    a hand piece comprising a body and a plunger adapted to reciprocate in the body;
    a cartridge comprising a chamber in the cartridge and a nozzle on a distal end of the cartridge, the chamber adapted to hold an intraocular lens, the nozzle having a hollow interior connected to the chamber, the cartridge adapted to fit into the hand piece; and
    a heater for heating the intraocular lens while the intraocular lens is external to an eye; and
    an indicator on the hand piece operable to be illuminated to display a visible indication to deliver the intraocular lens into the eye while the intraocular lens is external to the eye when the heater has heated the intraocular lens to a predetermined temperature range.

15. The intraocular lens delivery system of claim 14 wherein the heater is located on the cartridge.

16. The intraocular lens delivery system of claim 14 wherein the cartridge is made of a polymer and the heater is molded into the polymer.

17. The intraocular lens delivery system of claim 14 wherein the heater is located on the body.

18. The intraocular lens delivery system of claim 14 wherein the body is made of a polymer and the heater is molded into the polymer.

19. The intraocular lens delivery system of claim 14 wherein the heater is located on the plunger.

20. The intraocular lens delivery system of claim 14 wherein the plunger is made of a polymer and the heater is molded into the polymer.

21. The intraocular lens delivery system of claim 14 further comprising a power source for providing power to the heater.

22. The intraocular lens delivery system of claim 21 wherein the power source is a battery.

23. The intraocular lens delivery system of claim 14 further comprising a controller for regulating the temperature of the intraocular lens.

24. The intraocular lens delivery system of claim 23 further comprising an interface between the heater and the controller.

25. The intraocular lens delivery system of claim 24 wherein the interface provides feedback to the controller so that the controller can operate the heater to maintain the intraocular lens within a desired temperature range.

26. The intraocular lens delivery system of claim 14 further comprising a motor for moving the plunger.

27. The intraocular lens delivery system of claim 14 further comprising a spring for moving the plunger.

28. The intraocular lens delivery system of claim 14 further comprising a switch for activating the heater.

29. A device for delivering an intraocular lens into an eye comprising:
an injector body;
an indicator disposed on the injector body;
a plunger slidably movable within the injector body;
a nozzle portion located near a distal end of the injector body, the nozzle portion having a hollow interior capable of holding an intraocular lens;
a heater located near the intraocular lens and adapted to heat the intraocular lens while the intraocular lens is external to an eye;
a power source for providing power to the heater;
a controller for controlling the operation of the heater and for generating a signal to deliver the intraocular lens; and
an interface between the heater and the controller;
wherein the controller is adapted to regulate the temperature of the intraocular lens and to generate a signal to illuminate the indicator and deliver the intraocular lens into the eye while the intraocular lens is external to the eye in response to the temperature of the intraocular lens having been regulated such that the intraocular lens has been heated to a predetermined temperature range.

* * * * *